US011145009B2

(12) United States Patent
Weiss

(10) Patent No.: US 11,145,009 B2
(45) Date of Patent: Oct. 12, 2021

(54) METHOD FOR SUPPORTING A USER IN AN AGRICULTURAL ACTIVITY

(71) Applicant: 365FarmNet Group KGaA mbH & Co. KG, Harsewinkel (DE)

(72) Inventor: Philipp Weiss, Berlin (DE)

(73) Assignee: 365FARMNET GROUP KGAA MBH & CO. KG, Harsewinkel (DE)

( * ) Notice: Subject to any disclaimer, the term of this patent is extended or adjusted under 35 U.S.C. 154(b) by 0 days.

(21) Appl. No.: 17/015,180

(22) Filed: Sep. 9, 2020

(65) Prior Publication Data

US 2021/0090184 A1 Mar. 25, 2021

(30) Foreign Application Priority Data

Sep. 20, 2019 (DE) .......................... 102019125348.9

(51) Int. Cl.
*G06Q 50/02* (2012.01)
*G16H 15/00* (2018.01)
(Continued)

(52) U.S. Cl.
CPC ............. *G06Q 50/02* (2013.01); *G06Q 10/10* (2013.01); *G06T 11/00* (2013.01); *G16H 15/00* (2018.01); *H04W 4/029* (2018.02); *H04W 4/20* (2013.01)

(58) Field of Classification Search
CPC ........ G06Q 50/02; G06Q 10/10; G16H 15/00; G06T 11/00; H04W 4/029; H04W 4/20
See application file for complete search history.

(56) References Cited

U.S. PATENT DOCUMENTS

2016/0140728 A1* 5/2016 Aonuma ............. G02B 27/017
382/103
2017/0083024 A1* 3/2017 Reijersen Van Buuren ................
G05D 1/0094
(Continued)

FOREIGN PATENT DOCUMENTS

DE 102014103195 A1 9/2015
DE 102016215199 A1 3/2017
(Continued)

OTHER PUBLICATIONS

Santana-Fernández, Javier, Jaime Gómez-Gil, and Laura del-Pozo-San-Cirilo. "Design and implementation of a GPS guidance system for agricultural tractors using augmented reality technology." Sensors 10.11 (2010): 10435-10447. (Year: 2010).*
(Continued)

*Primary Examiner* — Xin Sheng
(74) *Attorney, Agent, or Firm* — Collard & Roe, P.C.

(57) ABSTRACT

A method for supporting a user in an agricultural activity with a control arrangement that has a mobile device and a server application which communicates with the mobile device. The control arrangement executes an augmented reality routine in which a real-world image generated by a camera and at least one item of added information are displayed in a visually superimposed manner on the mobile device. The server application has a plurality of application modules with which a predefined agricultural scenario is associated, and an amount of added information is stored in the database for each agricultural scenario. The control arrangement automatically determines in which of the predefined agricultural scenarios the mobile device is situated, and a partial amount of the amount of added information stored in the database for the determined agricultural sce-
(Continued)

nario is shown on the display depending on at least one object depicted in the real-world image.

15 Claims, 4 Drawing Sheets

(51) Int. Cl.
  *G06Q 10/10* (2012.01)
  *G06T 11/00* (2006.01)
  *H04W 4/029* (2018.01)
  *H04W 4/20* (2018.01)

(56) References Cited

U.S. PATENT DOCUMENTS

| | | | |
|---|---|---|---|
| 2017/0090196 A1 | 3/2017 | Hendron | |
| 2017/0097413 A1* | 4/2017 | Gillian | G01S 13/86 |
| 2017/0124776 A1 | 5/2017 | Carpentier et al. | |
| 2017/0140457 A1* | 5/2017 | Kaku | G06F 1/163 |
| 2017/0161569 A1* | 6/2017 | Ren | G08G 1/16 |
| 2017/0322715 A1* | 11/2017 | Cohrt | G06F 3/011 |
| 2018/0088663 A1* | 3/2018 | Zhang | G06K 9/00389 |
| 2018/0088677 A1* | 3/2018 | Zhang | G06F 3/0304 |
| 2018/0131907 A1* | 5/2018 | Schmirler | G05B 23/0216 |
| 2018/0150070 A1* | 5/2018 | Johnson | G06T 7/001 |
| 2018/0189568 A1* | 7/2018 | Powderly | G06T 7/70 |
| 2018/0369872 A1* | 12/2018 | McGarvey | G06K 9/3216 |
| 2019/0147655 A1* | 5/2019 | Galera | G05B 19/4061 345/419 |
| 2020/0026086 A1 | 1/2020 | Hendron | |

FOREIGN PATENT DOCUMENTS

| | | | | |
|---|---|---|---|---|
| EP | 3166054 A1 | 5/2017 | | |
| WO | WO-2015135786 A1 * | 9/2015 | | G02B 27/017 |
| WO | 2015/161307 A1 | 10/2015 | | |

OTHER PUBLICATIONS

European Search Report dated Dec. 14, 2020 issued in European Application No. 20 18 6161 (with English translation of the relevant parts).

* cited by examiner

METHOD FOR SUPPORTING A USER IN AN AGRICULTURAL ACTIVITY

CROSS-REFERENCE TO RELATED APPLICATIONS

This application claims priority under 35 USC 119 of German Application No. DE 10 2019 125 348.9, filed on Sep. 20, 2019, the disclosure of which is herein incorporated by reference.

BACKGROUND OF THE INVENTION

The invention is directed to a method for supporting a user in an agricultural activity, a mobile device configured for use in the suggested method, and a server application configured for use in the suggested method.

Diverse agricultural activities are presently being performed in a data-based manner. Augmented reality routines represent one possibility for supporting farmers and other users in such activities. These augmented reality routines are usually carried out with the aid of mobile devices and are frequently supported by server applications. Due to the high complexity of both the data and the activities, it is advantageous when the user is supported by the augmented reality routine in the most intuitive and simple manner possible.

It is known from the prior art (DE 10 2014 103 195 A1, DE 10 2016 215 199 A1, EP 3 166 054 A1) to make use of mobile devices to superimpose added information on real-world imagery generated by a camera on a display of the mobile device in the manner of an augmented reality routine. It is also known from the prior art to carry out such augmented reality routines in an agricultural context. However, there is a large number of conceivable agricultural scenarios in which the user can be supported by means of augmented reality routines. These agricultural scenarios sometimes have very few commonalities. Correspondingly, the added information to be displayed and the necessary calculations for the respective scenario also vary widely. Therefore, an augmented reality routine which covers every agricultural scenario is hardly possible. Heretofore, augmented reality routines have therefore referenced individual agricultural scenarios but were not intended to support the user comprehensively in as many agricultural scenarios as possible.

SUMMARY OF THE INVENTION

The invention is based on the problem of configuring and further developing the known method in such a way that it can be used as flexibly as possible in different agricultural scenarios with the least possible complexity.

The above-stated problem is solved in a for supporting a user in an agricultural activity by means of a control arrangement, wherein the control arrangement has at least one mobile device and a server application which communicates with the mobile device and which has a database. The mobile device has a camera and a display, wherein an augmented reality routine is executed by the control arrangement. In the augmented reality routine, a real-world image generated by the camera and at least one item of added information which is stored in the database and which is associated with an agricultural scenario are displayed in a visually superimposed manner on the display of the mobile device. The respective added information is associated with at least one real-world object depicted in the real-world image. The server application comprises a plurality of application modules with which a predefined agricultural scenario is associated in each instance, and an amount of added information is stored in the database for each agricultural scenario. The control arrangement automatically determines in which of the predefined agricultural scenarios the mobile device is situated, in that the amount of added information stored in the database is determined by the control arrangement depending on the determined agricultural scenario. A partial amount of the amount of added information stored in the database for the determined agricultural scenario is shown on the display depending on at least one object depicted in the real-world image.

A key fundamental consideration consists in that a control arrangement having at least one mobile device and a server application communicating with the mobile device is configured such that it automatically determines the agricultural scenario in which the mobile device is situated. For this purpose, the server application comprises a plurality of application modules, each of which is associated with an agricultural scenario. Examples which will be explained more fully later include a "field inspection" agricultural scenario, a "livestock inspection" agricultural scenario and a "field cultivation" agricultural scenario. The user can then be specifically supported through the interplay between the mobile device and the server application depending on the respective agricultural scenario.

In particular, it is suggested that the server application comprises a plurality of application modules with which a predefined agricultural scenario is associated in each instance, and an amount of added information is stored in the database for every agricultural scenario, in that the control arrangement automatically determines in which of the predefined agricultural scenarios the mobile device is situated, and the amount of added information stored in the database is determined by the control arrangement depending on the determined agricultural scenario. A partial amount of the amount of added information stored in the database for the determined agricultural scenario is displayed on the display depending on at least one object depicted in the real-world imagery.

The suggested method accordingly has the advantage that the user is not flooded with an amount of added information that is not needed by the user at a particular point in time and, therefore, the control arrangement need not simultaneously execute a large quantity of calculations, the results of which would be irrelevant for the user at that particular time. This makes it possible for the first time to support the user in a needs-based manner in a variety of agricultural scenarios without increasing the complexity for the user.

In the preferred configuration, identification conditions are associated with the application modules in each instance and are collated with identification information associated with the mobile device in order to determine the agricultural scenario in which the mobile device is situated. Even a small amount of identification information may be sufficient to rule out many agricultural scenarios or to directly determine the current agricultural scenario. Accordingly, the agricultural scenario in which the mobile device is situated is automatically determined quickly using only minimal computing power. At the same time, this makes it possible to support the user in a multitude of potential agricultural scenarios without it being impossible or very time-consuming to select the actually current agricultural scenario.

In a further preferred configuration, the identification conditions comprise the presence of identification objects in the real world. For example, an animal-specific agricultural scenario can be quickly deduced from the presence of specific animals as identification objects, while a harvest-specific agricultural scenario can be deduced from the presence of a combine harvester and an agricultural field which is ready to be harvested as identification objects.

For example, in order to determine the presence of an agricultural work machine in an uncomplicated manner, it is suggested in the configuration that the mobile device be connected to at least one real-world object via a radio link. The presence of the radio link itself, but also identification information transmitted via the radio link, can be utilized to determine the agricultural scenario.

In conventional augmented reality routines, the real-world objects which could potentially be present in the environment of the mobile device are frequently determined by the control arrangement only via image recognition. In the present case, however, it was realized that the amount of potential radio links in agricultural scenarios is very small compared with the amount of potential objects to be recognized through image recognition. Moreover, since the detection of a radio link and the transmission of data via this radio link requires less computing power than image recognition, the inclusion of the radio link in the determination of the agricultural scenario represents a very good option for quickly limiting the amount of potential agricultural scenarios.

The preferred "field inspection", "livestock inspection" and "field cultivation" agricultural scenarios particularly benefit from the possibilities for support by means of augmented reality routines, while the added information therein which is required by the user varies appreciably at the same time. The user can accordingly be supported in a scenario-specific manner in each of the agricultural scenarios by automatically determining in which of these predefined agricultural scenarios the mobile device is situated.

The mobile device can be a smartphone or a tablet or a mobile phone or a head-up display of an agricultural work machine or data goggles, and/or the camera is installed in the mobile device.

The user can modify the displayed added information through input in the mobile device. This can be simple information, for example, the feeding of an animal, which is accordingly stored in the database. In an equally advantageous manner, it can be provided that the user can input complex planning directly on-site. In this way, the user can fully exploit the advantages of augmented reality.

In the field inspection scenario, the user aims the camera at a specific field and the control arrangement determines the presence of a general field as identification information, and/or in that position information of the mobile device is determined as identification information by the control arrangement, particularly via GPS. Since generally many of the agricultural scenarios can occur only at determined locations, position information of the mobile device in particular acquires major importance as identification information.

In one embodiment, the user aims the camera at at least one specific animal, and the presence of a general animal is determined by the control arrangement as identification information, and/or the mobile device is connected via a radio link, in particular via RFID, to a connected object associated with the animal. Preferably, it is determined by the control arrangement that the mobile device is situated in the "livestock inspection" agricultural scenario based on the identification information, further preferably in that the specific animal from a quantity of predefined specific animals that is stored in the database is determined by the control arrangement, particularly based on the radio link and, depending on the specific animal, the amount of potential added information stored in the database is determined by the control arrangement.

Particularly noteworthy in this respect is the fact that farm animals are often identified by RFID tags, the presence of which by itself already supplies much information and allows additional inferences to be made about the specific animal.

When the control arrangement determines that the mobile device is situated in the "field cultivation" agricultural scenario, the control arrangement determines from this that the mobile device is also situated in the "field inspection" agricultural scenario.

In one embodiment, the application modules comprise at least one application module associated with the "field inspection" agricultural scenario and/or an application module associated with the "livestock inspection" agricultural scenario and/or an application module associated with the "field cultivation" agricultural scenario. In addition or alternatively, the application modules are supplied by different manufacturers, and/or in the user can preselect different application modules, and the predefined agricultural scenarios are associated with the preselected application modules.

In a further embodiment, a mobile device is configured for use in the suggested method. Reference is made to all of the statements relating to the suggested method.

In a further teaching a server application is configured for use in a suggested method. Reference is made to all of the statements relating to the suggested method.

BRIEF DESCRIPTION OF THE DRAWINGS

The invention will be described in more detail referring to drawings depicting only one embodiment example. In the drawings.

DETAILED DESCRIPTION OF THE EMBODIMENTS

Figure 1:
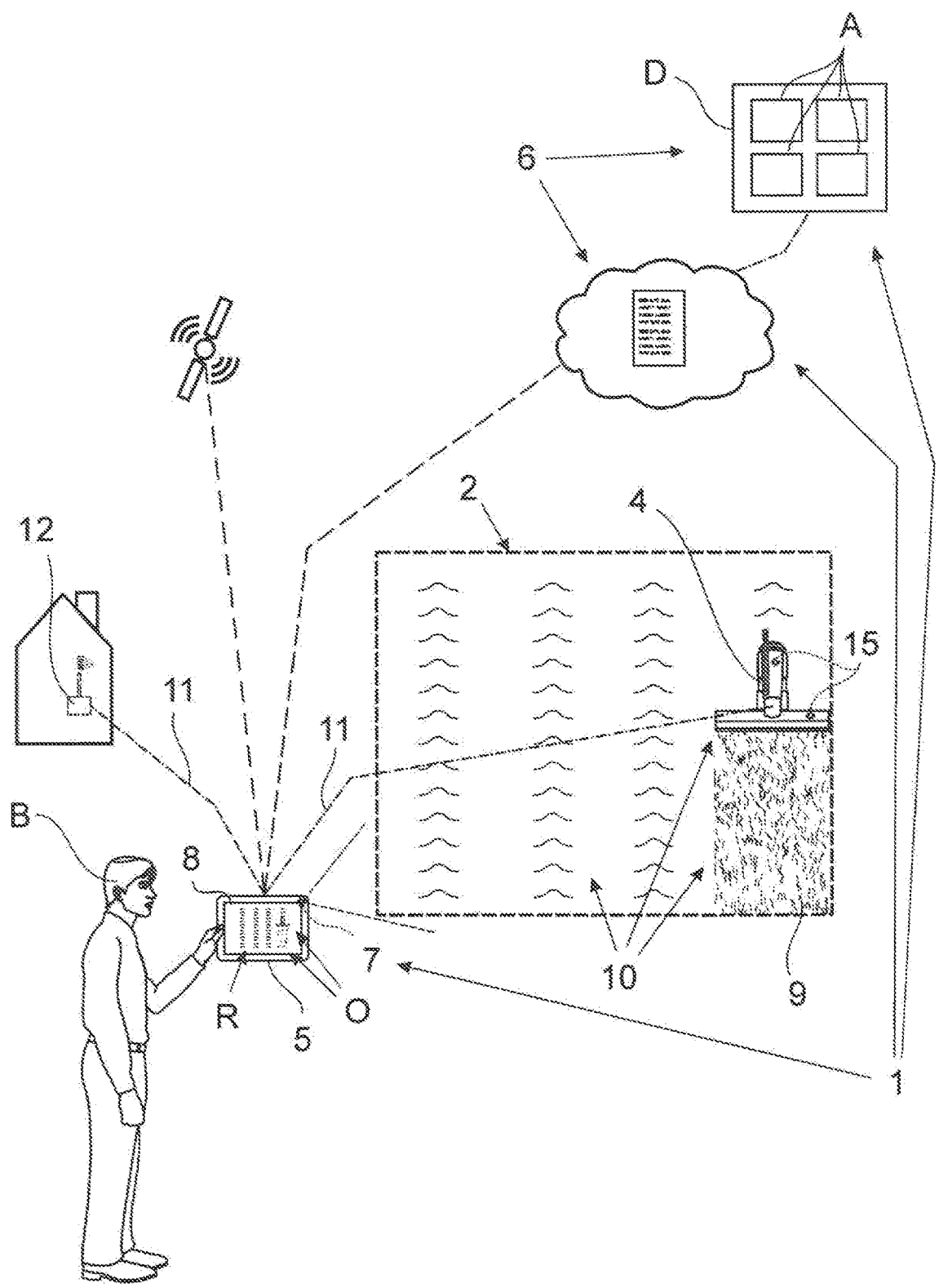
FIG. 1 shows a suggested method in use in a field.

FIG. 1 schematically shows a possible use of the suggested method for the support of a user B in an agricultural activity. The user B is supported in this instance by means of a control arrangement 1. The term "agricultural activity" is to be understood broadly and includes any activity relating to goal-driven production of vegetable and/or animal products. Some examples of agricultural activity are inspection of a field 2 or inspection of livestock 3, harvesting the field 2, plowing the field 2 or servicing of an agricultural work machine 4.

The control arrangement 1 has at least one mobile device 5 and a server application 6 which communicates with the mobile device 5 and which has a database D. The term "server application" is not to be understood in a narrow sense as a computer program but rather also comprises one or more servers on which a corresponding computer program is executed and on which the database D can be stored.

The mobile device 5, which is a tablet in the embodiment example shown in the drawings, has a camera 7 and a display 8. Further preferred embodiment forms of the mobile device 5 are mentioned in the following.

An augmented reality routine is executed by the control arrangement 1. Known means, for example, ARCore, can be used for this purpose. In the augmented reality routine, a real-world image R generated by the camera 7 and at least one item of added information Z which is stored in the database D and which is associated with an agricultural scenario are displayed in a visually superimposed manner on the display 8 of the mobile device 5. The real-world image R is usually normal video data. However, it can also be a photograph or processed video data. In the present case and preferably, it is live video data.

The respective added information Z is associated with at least one real-world object O depicted in the real-world image R. For example, the real-world object O depicted in the real-world image R can be an imaged animal, an imaged plant or an imaged portion of a field 2.

It is suggested that the server application 1 comprises a plurality of application modules A with which a predefined agricultural scenario is associated in each instance. An amount of added information Z is stored in the database D for each agricultural scenario.

The control arrangement 1 automatically determines in which of the predefined agricultural scenarios the mobile device 5 is situated. This automatic determination can save the user B from having to choose one or more of the application modules A every time an agricultural scenario changes, possibly even when it is not known which of the application modules A will provide the user B with the required added information Z.

The amount of added information Z stored in the database D is determined by the control arrangement 1 depending on the determined agricultural scenario. In this respect, it can be provided that all of the added information Z stored in the database D is associated with one application module A so that the control arrangement 1 can easily determine the added information Z relevant for the determined agricultural scenario.

Particularly to prevent an excessive amount of added information Z not useful to the user B at the respective time from being displayed to the user B, a partial amount of the amount of added information Z stored in the database D for the determined agricultural scenario is shown on the display 8 depending on at least one object O depicted in the real-world image R. An image recognition routine, for example, which identifies at least some of the objects O depicted in the real-world image R can be provided for determining the partial amount. Options which are usable alternatively or additionally for identifying the depicted objects O are described in the following.

Accordingly, the suggested method is characterized by its two-stage character. It is first determined in which of the predefined agricultural scenarios the mobile device 5 is situated, and then the user B is supported depending on the agricultural scenario. However, it is not ruled out in this respect that the method entirely or partially repeats consecutively. In particular, a change of agricultural scenario can take place seamlessly.

It can be provided that the suggested method and/or the augmented reality routine is initiated automatically and/or by the user B. For example, the user B can move with the mobile device 5 within an agricultural context and can activate an app on the mobile device 5 that is associated with the augmented reality routine, whereupon it is then determined automatically in which of the predefined agricultural scenarios the mobile device 5 is situated. The term "agricultural scenario" refers broadly to various agricultural application contexts which are selected, in the present instance and preferably, from the group comprising an inspection of livestock 3, an inspection of a field crop 9 and a field cultivation, particularly with an agricultural work machine 4.

It is provided in the present instance and preferably that identification conditions are associated in each instance with the application modules A. These identification conditions can serve to determine in which of the predefined agricultural scenarios the mobile device 5 is situated. In this respect, it can be provided that the same agricultural scenario is associated with a plurality of application modules A. In this case, the determination of the partial amount of the amount of added information Z stored in the database D for the determined agricultural scenario acquires a greater importance because the amount of added information Z which can potentially be displayed in the agricultural scenario is increased by the plurality of application modules A. However, it can also be provided in an equally advantageous manner that exactly one agricultural scenario is associated with each application module A and/or each agricultural scenario is associated with exactly one application module A.

In the present instance and preferably, identification information associated with the mobile device 5 is determined by the control arrangement 1 and is collated with the identification conditions. Based on the results of the collation, it is determined by the control arrangement 1 in which of the agricultural scenarios the mobile device 5 is situated.

In this respect, it can be provided, for example, that the identification conditions of a plurality of application modules A with which a small amount of agricultural scenarios is associated are satisfied so that it can then be determined from the intersection of the agricultural scenarios in which of the agricultural scenarios the mobile device 5 is situated. In this respect, it cannot be ruled out that the mobile device 5 is situated in a plurality of agricultural scenarios simultaneously.

In the present instance and preferably, the identification conditions comprise the presence of real-world identification objects 10. Real-world objects present in the environment of the mobile device 5 can then be determined by the control arrangement 1 as identification information. These identification objects 10 can be real plants, animals, machines, buildings and so forth.

It is known in principle to detect diverse real-world objects in the real-world image R in an augmented reality context by means of image recognition. However, the larger the amount of application modules A in the suggested method, the more time-consuming the identification of the agricultural scenario. Upward of a certain amount of application modules A, it may even be impossible to determine the agricultural scenario at the given computing power within an acceptable time only via image recognition. However, there is always a substantial but manageable amount of objects in the agricultural context that are capable of forming radio links 11. These objects are spread over the various agricultural scenarios and can therefore serve as identification objects 10. Therefore, in the present instance and preferably, the mobile device 5 is connected to at least one real-world object 4, 12, 13, 14 via a radio link 11. This real-world object is preferably an agricultural work machine 4 and/or a WLAN router 12 and/or an NCF tag 13 and/or an RFID tag 14. In the present instance and preferably, the presence of the connected object 4, 12, 13, 14 as identification information is deduced by the control arrangement 1 based on the radio link 11.

It can also be provided that further identification information is transmitted to the mobile device 5 from the connected real-world object 4, 12, 13, 14 via the radio link 11. In particular, this further identification information can be object-specific data of the connected object 4, 12, 13, 14 and/or sensor data of sensors 15 of the connected object 4, 12, 13, 14. For example, sensor data which indicate that the agricultural work machine 4 is currently harvesting a field 2 could be transmitted from an agricultural work machine 4. It could be determined from this by the control arrangement 1 that the mobile device 5 is situated in an agricultural scenario in which a field 2 is harvested.

Three preferred agricultural scenarios are described in the following referring to FIGS. 2 to 4.

Figure 2:
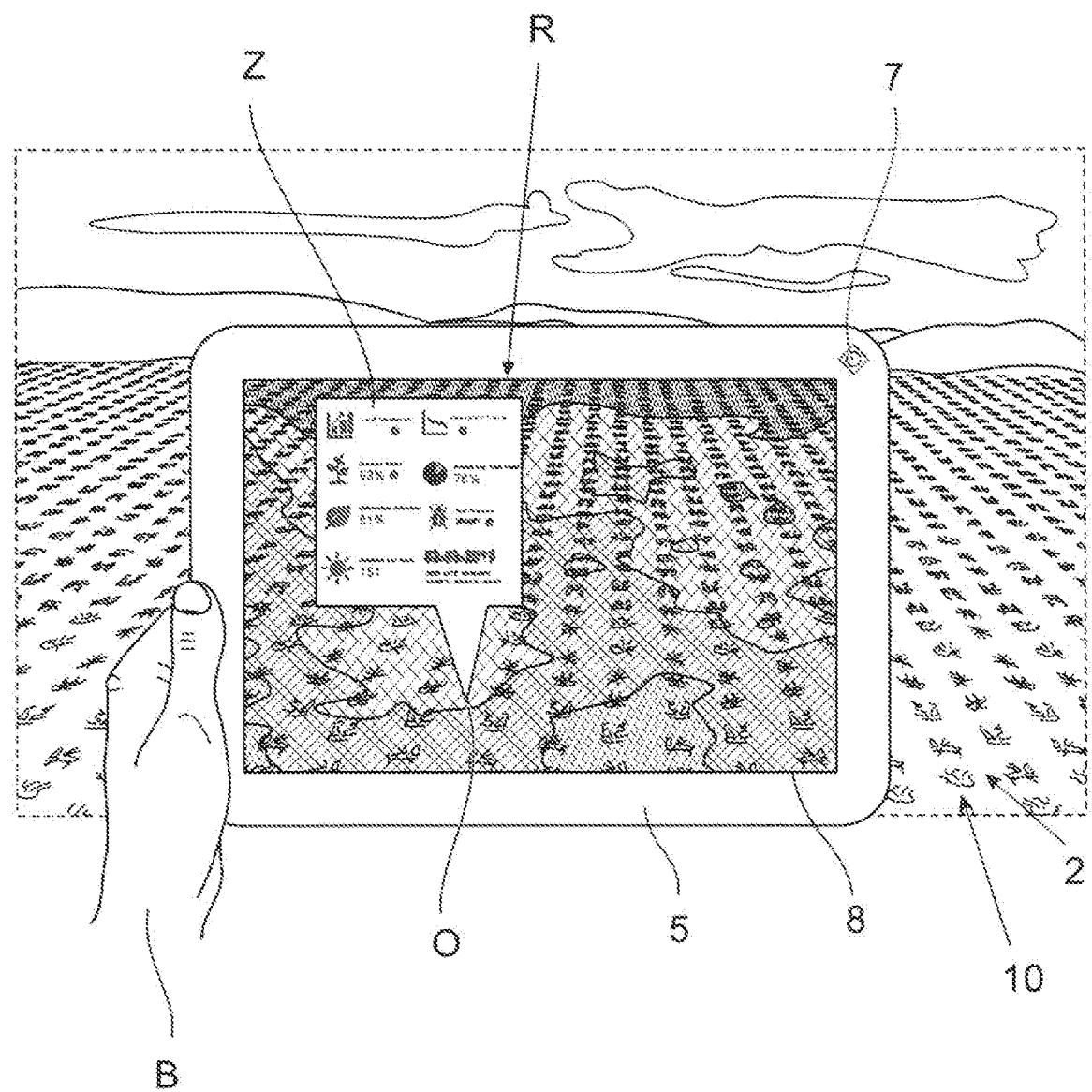
FIG. 2 shows the mobile device used in the suggested method in a field.

As is illustrated in FIG. 2, it can be provided that a "field inspection" agricultural scenario is an inspection of an agricultural field. Field data, particularly crop data and/or soil data and/or field development data and/or field development expectation data and/or biomass data and/or plant health data and/or chlorophyll saturation data and/or sunshine hours and/or pest infestation data are then preferably displayed as added information Z. In the present instance and preferably, the field data are position-dependent. Accordingly, for example, the pest infestation data may vary considerably at different positions in the field 2 and may be displayed differently in a corresponding matter.

Figure 3:
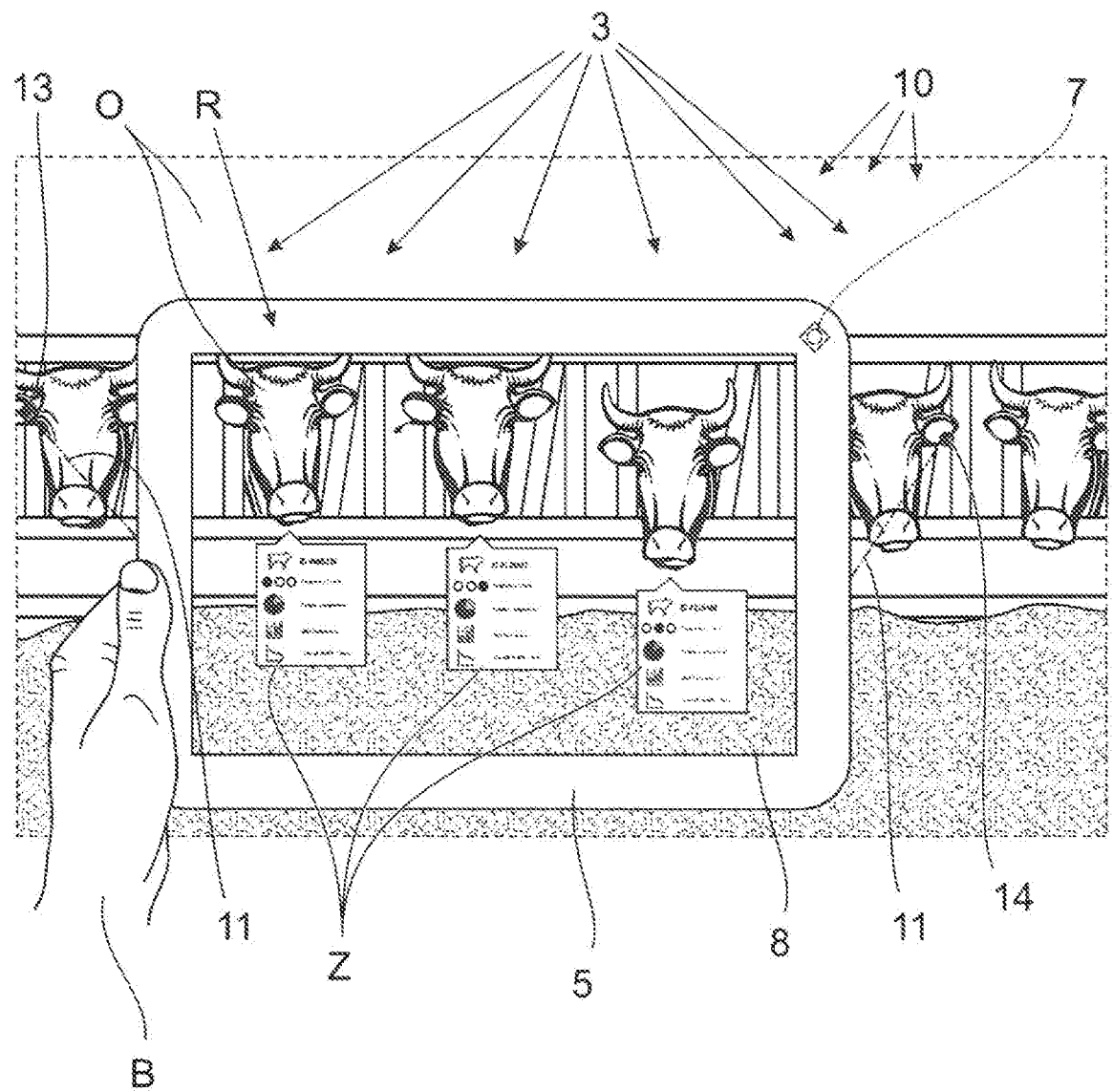
FIG. 3 shows the mobile device used in the suggested method in a stall.

Additionally or alternatively in the present instance and preferably, another agricultural scenario, "livestock inspection", shown in FIG. 3 is an inspection of livestock 3. In this regard, preferably individual data of a specific animal, in particular an animal ID and/or pregnancy data and/or feed composition data and/or milk output data and/or animal health data are preferably displayed as added information Z. Accordingly, the user B may be allowed to retrieve all relative data directly when tending to an animal.

Further additionally or alternatively, a "field cultivation" agricultural scenario can be cultivation of a field with an agricultural work machine 4. This is shown in FIG. 4. In this regard, field data, particularly crop data and/or soil data, particularly soil moisture, and/or machine data of the agricultural work machine 4, particularly a temperature and/or a planned route, are preferably displayed as added information Z.

As has already been mentioned, there are various possibilities by which the control arrangement 1 can determine the agricultural scenario in which the mobile device 5 is situated. Therefore, it can be provided that the mobile device 5 is connected to the agricultural work machine 4 via a radio link 11, particularly WLAN or Bluetooth, and the control arrangement 1 determines that the mobile device 5 is situated in the "field cultivation" agricultural scenario based on the radio link 11.

It follows from the dissimilarity of the above-mentioned agricultural scenarios that different mobile devices 5 can also be present in these agricultural scenarios. Accordingly, the mobile device 5 is preferably a smartphone or a tablet or a mobile phone or a head-up display of an agricultural work machine 4 or data goggles. It can be provided in general that the camera 7 is installed in the mobile device 5.

In the present instance and preferably, the mobile device 5 is moved by the user B during the augmented reality routine. The displayed real-world image R can change along with the depicted real-world object O so that the displayed added information Z also changes at the same time.

Further advantages of the suggested method result when the user B can make entries in the mobile device 5, the entries are associated with a depicted object O by the control arrangement 1, the displayed added information Z is modified by the control arrangement 1 based on the input, and the modified added information Z is stored in the database D. Accordingly it is possible for the user B not only to retrieve the added information Z on-site but also to carry out documentation on-site. It can be provided that the above-mentioned field data are modified in a position-dependent manner by the user's B input in the mobile device 5. For example, the user B can directly document a pest infestation in a position-dependent manner during the inspection of the agricultural field.

Additionally or alternatively, it can be provided that the individual data of the specific animal are modified through input of the user B in the mobile device 5. For example, the user B can document a feeding of an animal directly in an animal-specific manner.

Particularly at the start of the suggested method, it can be provided that the user B aims the camera 7 at a specific field 2 and the control arrangement 1 determines the presence of a general field 2 as identification information. Accordingly, it is possible in this case that the control arrangement 1 can deduce from the real-world image R merely that the camera 7 is aimed at a field 2 but cannot determine, or cannot directly determine, which field 2 of a quantity of potential fields 2 is being imaged.

It can then be provided additionally or alternatively that position information of the mobile device 5 is determined as identification information by the control arrangement 1, particularly via GPS.

Preferably, the control arrangement 1 determines that the mobile device 5 is situated in the "field inspection" agricultural scenario based on the identification information, particularly based on the presence of a general field 2 and/or field-specific identification objects 10, for example, the field crop 9, and/or based on the position information. This is illustrated in FIG. 2.

Further preferably, the specific field 2 from a quantity of predefined specific fields 2 stored in the database D is determined by the control arrangement 1 based on the identification information. Depending on the specific field 2, the amount of potential added information Z stored in the database D can then be determined by the control arrangement 1.

The specific field 2 in which the user B is located with the mobile device 5 can be determined in combination with the camera 7 and GPS. In this way, added information Z relating to this specific field 2 can be displayed to the user B. Especially with agricultural applications, the use of GPS makes it possible to draw concrete conclusions about the agricultural scenario in which the mobile device 5 is situated. Provided that the specific field 2 is among the quantity of predefined specific fields 2 stored in the database D and the position of the mobile device 5 is determined by means of GPS, the potential agricultural scenarios can immediately be limited to those relating to this specific field 2.

However, since agricultural scenarios do not extend only to fields 2, it can be provided that the user B aims the camera 7 at at least one specific animal, and the presence of a general animal is determined by the control arrangement 1 as identification information. Since the specific animal may possibly not be identifiable by means of image recognition without a large expenditure of time, similar to the specific field 2, it can be provided that the mobile device 5 is connected via a radio link 11, in particular by an RFID, to a connected object 13, 14 associated with the animal. This is possible because animals of agricultural livestock 3 are often identified by RFID tags 14.

Preferably, it is determined by the control arrangement 1 that the mobile device 5 is situated in the "livestock inspection" agricultural scenario depicted in FIG. 3 based on the identification information, particularly the presence of the general animal and/or the presence of the connected object 13, 14 and/or the radio link 11. Further preferably, the specific animal from a quantity of predefined specific animals that is stored in the database D is determined by the control arrangement 1, particularly based on the radio link 11 and, depending on the specific animal, the amount of potential added information Z stored in the database D is preferably determined by the control arrangement 1.

Figure 4:
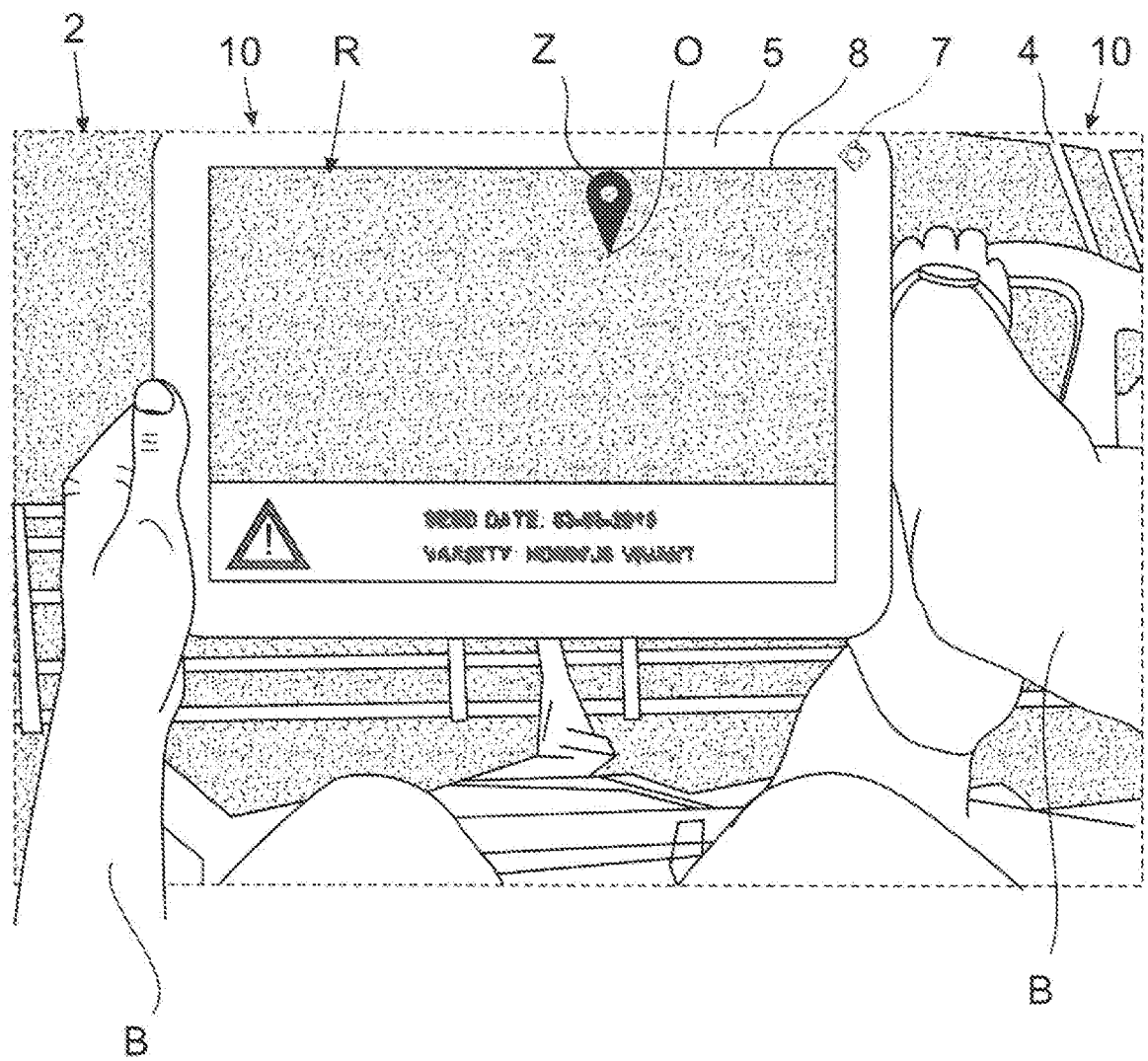
FIG. 4 shows the mobile device used in the suggested method in the cultivation of a field.

The "field cultivation" agricultural scenario shown in FIG. 4 can preferably be plowing a field 2, sowing seed, harvesting the field crop 9, or the like. Added information Z about the field 2 as well as added information Z associated with the agricultural machine 4 are important for the user B. Added information concerning the specific activity may also be relevant in this case.

As has already been stated, the mobile device 5 can be situated in a plurality of agricultural scenarios simultaneously. Therefore, in the above-mentioned agricultural scenarios it can be provided that the control arrangement 1 determines that the mobile device 5 is situated in the "field cultivation" agricultural scenario, and the control arrangement 1 determines from this that the mobile device 5 is also situated in the "field inspection" agricultural scenario. In this respect, however, it can be provided that not all of the added information Z that would be displayed in the "field inspection" agricultural scenario if the mobile device 5 were not also situated in the "field cultivation" agricultural scenario at the same time is also displayed when the mobile device 5 is simultaneously situated in the "field cultivation" agricultural scenario.

In general, the application modules A preferably comprise at least one application module A associated with the "field inspection" agricultural scenario and/or an application module A associated with the "livestock inspection" agricultural scenario and/or an application module A associated with the "field cultivation" agricultural scenario.

Because of the high flexibility of the suggested method, it can be provided that the application modules A are supplied by different manufacturers. In other words, it is possible to provide the user B with a large variety of added information Z by means of a server application 6.

It can be provided in addition or alternatively that the user B can preselect many different application modules A and that the predefined agricultural scenarios are associated with the preselected application modules A. Accordingly, it can be advantageous that the control arrangement 1 does not detect any agricultural scenarios for which no preselected application modules A exist, since it is then possible that no displayable information Z exists either.

Generally, it is also preferably the case that at least two agricultural scenarios are provided which are only possible in different locations. Preferably, at least one agricultural scenario is a farmyard and another agricultural scenario is a field.

According to a further independent teaching which is to be considered as independent, a mobile device 5 is claimed which is configured for use in a suggested method. Reference is made to all of the statements relating to the suggested method. The mobile device 5 can have, in particular, an app with access information enabling communication with the server application 6.

According to a further independent teaching which is likewise to be considered as independent, a server application 6 is claimed which is configured for use in a suggested method. Reference is made to all of the statements relating to the suggested method. In the server application 6, an independent standing is attributed particularly to a software separate from the hardware. At the same time, hardware which is configured for use in the suggested method is also to be considered as independent.

The suggested software can comprise the database D or can be configured to communicate with a database D.

REFERENCE CHARACTERS 1 control arrangement
2 FIELD
3 livestock
4 agricultural work machine
5 mobile device
6 server application
7 camera
8 display
9 field crop
10 identification objects
11 radio link
12 WLAN router
13 NFC tag
14 RFID tag
15 sensors
B user
D database
R real-world image
Z added information
O depicted object
A application module

What is claimed is:

1. A method for supporting a user in an agricultural activity by means of a control arrangement, wherein the control arrangement has at least one mobile device and a server application which communicates with the mobile device and which has a database, wherein the mobile device has a camera and a display, comprising executing with the control arrangement an augmented reality routine by performing the following steps:

displaying in a visually superimposed manner on the display of the mobile device a real-world image generated by the camera and at least one item of added information which is stored in the database and which is associated with an agricultural scenario, associating the respective added information with at least one real-world object depicted in the real-world image, wherein the server application comprises a plurality of application modules with which a predefined agricultural scenario is associated, storing an amount of added information in the database for each agricultural scenario, automatically determining with the control arrangement in which of the predefined agricultural scenarios the mobile device is situated, determining with the control arrangement the amount of added information stored in the database depending on the determined agricultural scenario, and displaying on the display a partial amount of the amount of added information stored in the database for the determined agricultural scenario, depending on at least one object depicted in the real-world image.

2. The method according to claim 1, wherein identification conditions are associated with the application modules, wherein identification information associated with the mobile device is determined by the control arrangement and is correlated with the identification conditions, and wherein, based on the results of the correlation, the control arrangement determines in which of the agricultural scenarios the mobile device is situated.

3. The method according to claim 2, wherein the identification conditions comprise the presence of real-world identification objects, and wherein real-world objects present in the environment of the mobile device are determined by the control arrangement as identification information.

4. The method according to claim 2, wherein the mobile device is connected via a radio link to at least one real-world object, wherein the presence of the connected real-world object as identification information is deduced by the control arrangement based on the radio link, and wherein further identification information in the form of object-specific data of the connected real-world object or sensor data of sensors of the connected real-world object, is transmitted to the mobile device from the connected real-world object via the radio link.

5. The method according to claim 1, wherein a "field inspection" agricultural scenario is an inspection of an agricultural field, wherein field data in the form of crop data or soil data or field development data or field development expectation data or biomass data or plant health data or chlorophyll saturation data or sunshine hours or pest infestation data are displayed as added information, and wherein the field data are position-dependent.

6. The method according to claim 5, wherein the user aims the camera at a specific field and the control arrangement determines the presence of a general field as identification information, and wherein position information of the mobile device is determined as identification information by the control arrangement via GPS, wherein the control arrangement determines that the mobile device is situated in the "field inspection" agricultural scenario based on the identification information, and wherein the specific field from a quantity of predefined specific fields stored in the database is determined by the control arrangement based on the identification information and, depending on the specific field, the amount of potential added information stored in the database is determined by the control arrangement.

7. The method according to claim 1, wherein a "livestock inspection" agricultural scenario is an inspection of livestock, and wherein individual data of a specific animal, in the form of an animal ID or pregnancy data or feed composition data or milk output data or animal health data are displayed as added information.

8. The method according to claim 7, wherein the user aims the camera at at least one specific animal, and the presence of a general animal is determined by the control arrangement as identification information, and the mobile device is connected via a radio link to a connected object associated with the animal, wherein the control arrangement determines that the mobile device is situated in the "livestock inspection" agricultural scenario based on the identification information, and that a specific animal from a quantity of predefined specific animals that is stored in the database is determined by the control arrangement based on the radio link and, depending on the specific animal, the amount of potential added information stored in the database is determined by the control arrangement.

9. The method according to claim 1, wherein a "field cultivation" agricultural scenario is a cultivation of a field with an agricultural work machine, wherein field data in the form of crop data or soil data, including soil moisture, machine data of the agricultural work machine, a temperature or a planned route, are displayed as added information, and wherein the mobile device is connected to the agricultural work machine via a radio link and the control arrangement determines that the mobile device is situated in the "field cultivation" agricultural scenario based on the radio link.

10. The method according to claim 9, wherein the control arrangement determines that the mobile device is situated in a "field cultivation" agricultural scenario, and the control arrangement determines from that the mobile device is also situated in the "field inspection" agricultural scenario.

11. The method according to claim 1, wherein the mobile device is a smartphone or a tablet or a mobile phone or a head-up display of an agricultural work machine or data goggles and wherein the camera is installed in the mobile device.

12. The method according to claim 1, wherein the user makes entries in the mobile device, wherein the entries are associated with a depicted object by the control arrangement, the displayed added information is modified by the control arrangement based on the entries, and the modified added information is stored in the database, wherein field data are modified in a position-dependent manner by the user's input in the mobile device, and wherein individual data of a specific animal are modified through input of the user in the mobile device.

13. The method according to claim 1, wherein the application modules comprise at least one application module associated with a "field inspection" agricultural scenario and/or an application module associated with a "livestock inspection" agricultural scenario and/or an application module associated with a "field cultivation" agricultural scenario, and wherein the application modules are supplied by different manufacturers, wherein user can preselect different application modules, and wherein the predefined agricultural scenarios are associated with the preselected application modules.

14. A mobile device configured for use in a method according to claim 1.

15. A server application configured for use in a method according claim 1.

* * * * *